United States Patent [19]

Maekawa et al.

[11] Patent Number: 5,646,222
[45] Date of Patent: Jul. 8, 1997

[54] POLYFLUOROHYDROCARBON GROUP-CONTAINING MONOMERS, THEIR POLYMERS AND APPLICATIONS OF THE POLYMERS

[75] Inventors: Takashige Maekawa; Ryoko Osawa; Satoshi Kamata; Seisaku Kumai, all of Yokohama, Japan

[73] Assignee: Asahi Glass Company Ltd., Tokyo, Japan

[21] Appl. No.: 682,010

[22] Filed: Jul. 16, 1996

Related U.S. Application Data

[62] Division of Ser. No. 394,207, Feb. 24, 1995, Pat. No. 5,565,607, which is a continuation of Ser. No. 83,534, Jun. 30, 1993, abandoned.

[30] Foreign Application Priority Data

Jul. 3, 1992 [JP] Japan ................... 4-200680
Feb. 9, 1993 [JP] Japan ................... 5-044566

[51] Int. Cl.⁶ .................................................. C08F 12/30
[52] U.S. Cl. .................................................. 526/243
[58] Field of Search .................................................. 526/243

[56] References Cited

U.S. PATENT DOCUMENTS

| | | | |
|---|---|---|---|
| 2,826,564 | 3/1958 | Bovey et al. | 560/223 |
| 2,839,513 | 6/1958 | Ahlbrecht et al. | 560/223 |
| 3,514,420 | 5/1970 | Katsushima et al. | 560/223 |
| 3,660,360 | 5/1972 | Chaudhuri et al. | 560/223 |
| 3,716,577 | 2/1973 | Pittman et al. | 560/223 |
| 3,773,826 | 11/1973 | Rondestvedt . | |
| 3,949,112 | 4/1976 | Pattison | 568/843 |
| 4,080,507 | 3/1978 | Greshaw | 560/223 |
| 5,026,902 | 6/1991 | Fock et al. | 560/223 |

FOREIGN PATENT DOCUMENTS

| | | | |
|---|---|---|---|
| 61-10534 | 1/1986 | Japan | 560/223 |
| 61-180743 | 8/1986 | Japan | 560/223 |
| 1-305052 | 12/1989 | Japan | 560/223 |

OTHER PUBLICATIONS

Chemical Abstracts, 106:68426f, "35–Chemistry of Synthetic High Polymers", vol. 106, No. 10, 1987.
Chemical Abstracts, 115:48915x, "1–Pharmacology", vol. 115, No. 5, 1991.
JP 61-183377 English–translated version Aug. 16, 1986.
"Antitack Agents", JP61183377 16 Aug. 1986 by Hisamoto et al.

Primary Examiner—Joseph L. Schofer
Assistant Examiner—N. Sarofim
Attorney, Agent, or Firm—Oblon, Spivak, McClelland, Maier & Neustadt, P.C.

[57] ABSTRACT

A polyfluorohydrocarbon group-containing acrylate of the formula (1):

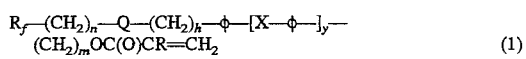

$$R_f-(CH_2)_n-Q-(CH_2)_h-\phi-[X-\phi-]_y-(CH_2)_m OC(O)CR=CH_2 \quad (1)$$

wherein $R_f$ is a polyfluorohydrocarbon group having from 2 to 22 carbon atoms to which fluorine atoms are bonded, wherein some of such carbon atoms may be substituted by ether-type oxygen atoms, $\phi$ is a p-phenylene group which may be substituted by one or more halogen atoms selected from fluorine and chlorine, provided that when a plurality of $\phi$ are present in one molecule, such a plurality of $\phi$ may be the same or different from one another, R is a hydrogen atom, a methyl group, a fluorine atom, a chlorine atom or a bromine atom, Q is an oxygen atom or a sulfur atom, X is a single bond, —CH=CH—, —N=CH—, —CH=N— or —C(O)—, n is an integer of from 1 to 22, h is an integer of from 0 to 22, m is an integer of from 1 to 11, and y is an integer of from 0 to 5.

14 Claims, No Drawings

POLYFLUOROHYDROCARBON GROUP-CONTAINING MONOMERS, THEIR POLYMERS AND APPLICATIONS OF THE POLYMERS

This is a Division of application Ser. No. 08/394,207 filed on Feb. 24, 1995, U.S. Pat. No. 5,565,607, which is a continuation of application Ser. No. 08/083,534 filed on Jun. 30, 1993, abandoned.

The present invention relates to novel polyfluorohydrocarbon group-containing acrylates, their polymers and agents containing such polymers as effective components.

Heretofore, polymers having polyfluoroalkyl groups have been known as water and oil repellants or surface modifiers. As monomers for such polymers, various polyfluoroalkyl group-containing acrylates are widely known including acrylic acid esters of polyfluoroalkylethyl alcohols. Polyfluoroalkyl group-containing monomers having a benzene ring are also known. Fluorine-containing monomers having two or more benzene rings are likewise known.

Heretofore, as polyfluoroalkyl group-containing monomers having a benzene ring, polyfluoroalkylstyrene derivatives ($CH_2$=CH—Ph—$CH_2$OCH$R^1R^2$, wherein Ph is a phenylene group) have been known. It is known to use such monomers wherein $R^1$ is a linear perfluoroalkyl group (see Japanese Unexamined Patent Publication No. 293943/1986) or such monomers wherein $R^1$ is a perfluoroalkylpolyether group for the purpose of improving the adhesion (see Japanese Unexamined Patent Publication No. 112938/1991). Further, methacrylate or acrylate-type monomers having specific structures having two or more benzene rings for the purpose of providing a nature of liquid crystal, are also known (see U.S. Pat. No. 5,087,672).

Polymers of these styrene-type monomers are essentially rigid polymers, since benzene rings are directly bonded to the main chains, and they are practically not adequate with respect to the adhesive properties or affinity to the base material. Further, such rigid main chain portions hinder the orientation of side chain portions, and especially when such polymers are used as surface modifiers, the surface modifying effects (especially the lasting effects) due to polyfluoroalkyl groups will not be at a satisfactory level.

On the other hand, as compared with such styrene-type monomers, acrylic monomers are capable of forming polymers having flexible main chain backbones. As compared with the polymers of styrene-type monomers, polymers of acrylic monomers can easily be improved with respect to the adhesive properties or affinity to the base material, but they are not yet adequate from the viewpoint of efficiently orienting the polyfluoroalkyl groups and effectively utilizing the surface modifying effects of fluorine atoms. Accordingly, a further improvement has been desired especially in the field of surface modifiers.

Further, the monomers disclosed in the above-mentioned U.S. Pat. No. 5,087,672 are designed to provide the nature of liquid crystal, and they are not designed to provide water and oil repellency as in the present invention. Furthermore, polymers containing a large amount of polymerized units of an acrylic monomer of this type, have poor solubility in a petroleum type solvent or in a hydrocarbon type solvent, which has been a problem when it has been attempted to commercialize them as solvent type or aqueous dispersion type surface modifiers. Further, when the surface modification of a resin is to be conducted by kneading a polymer of this type to a commonly used resin, the fluorine-containing polymer is usually poor in the compatibility, and it is usually difficult to incorporate it uniformly. Thus, there has been a problem that the expected effects can hardly be obtained.

It is an object of the present invention to solve such problems of the conventional polyfluoroalkyl group-containing polymers and to improve the water and oil repellency and its lasting effects, the adhesive properties and affinity to the base material, the solubility to hydrocarbon type solvents and the compatibility with commonly used resins. The present invention relates to a novel monomer capable of forming such a polymer, a polymer of such a monomer, a process for producing such a polymer and an agent containing such a polymer.

Namely, the present invention provides a polyfluorohydrocarbon group-containing acrylate of the formula (1):

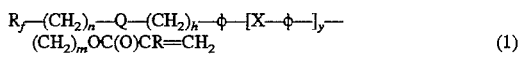

$$(CH_2)_mOC(O)CR=CH_2 \qquad (1)$$

wherein $R_f$ is a polyfluorohydrocarbon group having from 2 to 22 carbon atoms to which fluorine atoms are bonded, wherein some of such carbon atoms may be substituted by ether-type oxygen atoms, φ is a p-phenylene group which may be substituted by one or more halogen atoms selected from fluorine and chlorine, provided that when a plurality of φ are present in one molecule, such a plurality of φ may be the same or different from one another, R is a hydrogen atom, a methyl group, a fluorine atom, a chlorine atom or a bromine atom, Q is an oxygen atom or a sulfur atom, X is a single bond, —CH=CH—, —N=CH—, —CH=N— or —C(O)—, n is an integer of from 1 to 22, h is an integer of from 0 to 22, m is an integer of from 1 to 11, and y is an integer of from 0 to 5.

The present invention also provides a polymer of at least one type of the acrylate of the formula (1), or of at least one type of the acrylate of the formula (1) with at least one type of other monomers copolymerizable with the acrylate of the formula (1).

Further, the present invention provides a water and oil repellant or a surface modifier containing such a polymer as an effective component.

Now, the present invention will be described in detail with reference to the preferred embodiments.

For the polyfluorohydrocarbon group-containing acrylate of the present invention, various $R_f$ groups may be employed as the polyfluorohydrocarbon ($R_f$) group. This $R_f$ group is required to have from 2 to 22, preferably from 4 to 18, more preferably from 6 to 14, carbon atoms to which fluorine atoms are bonded. The number of fluorine atoms is preferably at least 60%, more preferably at least 80%, as represented by the ratio (the substitution ratio) of the number of fluorine atoms substituted to the number of hydrogen atoms of the corresponding non-substituted hydrocarbon group. Some or all of the rest of hydrogen atoms may be substituted by chlorine atoms. The most preferred $R_f$ group is a perfluorohydrocarbon group wherein all of hydrogen atoms of the non-substituted hydrocarbon group are substituted by fluorine atoms.

As the $R_f$ group, a polyfluoroalkyl group is preferred. This polyfluoroalkyl group may have a small number of branches, but is preferably a linear polyfluoroalkyl group. In the case of a branched polyfluoroalkyl group, the branched portion should preferably be a short chain and be located at the terminal or near the terminal of the polyfluoroalkyl group. The most preferred polyfluoroalkyl group is a linear perfluoroalkyl group of the formula $CF_3(CF_2)_k$— wherein k is an integer of from 1 to 21. The carbon number (k+1) of this particularly preferred linear perfluoroalkyl group is from 6 to 14.

Other than the polyfluoroalkyl group, the $R_f$ group may be a chain polyfluorohydrocarbon group having at least one unsaturated group such as a carbon-carbon unsaturated double bond. Further, the $R_f$ group may be a polyfluorooxalkyl group wherein some of carbon atoms of the polyfluoroalkyl group are substituted by ether-type oxygen atoms. Particularly preferred is a polyfluorooxalkyl group (particularly a perfluorooxalkyl group) having at least one perfluorooxypropylene group. Here, the carbon number is preferably from 6 to 18 inclusive of the carbon atoms substituted by the oxygen atoms.

The $R_f$ group includes, for example, the following specific $R_f$ groups, but it is not limited to such specific groups.
$CF_3(CF_2)_7$—, $CF_3(CF_2)_9$—, $CF_3(CF_2)_{11}$—,
$HCF_2(CF_2)_7$—, $ClCF_2(CF_2)_9$—, $CF_3(CF_2)_3(CH_2CH_2)$—,
$CF_3(CF_2)_3(CFClCF_2)_7$—, $(CF_3)_2CF(CF_2)_4$—, $CF_3CF=CFCF_2CF=CF$—,
$C_3F_7O$—$\{CF(CF_3)CF_2O\}_i$—$CF(CF_3)$— and
$C_3F_7O$—$\{CF(CF_3)CF_2O\}_i$—$(CF_2)_j$—, wherein i is an integer of from 1 to 4, and j is an integer of from 2 to 6.

φ is a p-phenylene group i.e. a 1,4-phenylene group. Some or all of four hydrogen atoms of this phenylene group may be substituted by halogen atoms selected from fluorine and chlorine. Preferred φ is a non-substituted p-phenylene group. When a plurality of φ are present in one molecule, such a plurality of φ may be the same or different. For example, in a compound having two φ in one molecule, one of φ may be a p-phenylene group, and the other φ may be a halogen-substituted p-phenylene group.

R is preferably a hydrogen atom or a methyl group. Namely, as the acrylate of the formula (1), an acrylate derivative or a methacrylate derivative is preferred. Further, Q is preferably an oxygen atom.

n is required to be an integer of from 1 to 22, and it is preferably from 1 to 11 from the viewpoint of the orientation of a polyfluorohydrocarbon group. More preferably, n is an integer of from 1 to 4. h is an integer of from 0 to 22, preferably from 0 to 4. More preferably, it is from 0 to 2, particularly 0 to 1, from the viewpoint of simple productivity. m is required to be an integer of from 1 to 11, preferably an integer of from 2 to 4. y showing the number of φ in one molecule is required to be an integer of from 0 to 5. Preferred y is from 0 to 1. When a plurality of φ are contained in one molecule, the connecting portion of two adjacent φ is X. X is a single bond, —CH=CH—, —N=CH—, —CH=N— or —C(O)—. Preferably, X is —CH=N— or —C(O)—.

The polyfluorohydrocarbon group-containing acrylate of the present invention can be prepared, for example, by the following method. Namely, it can be prepared by reacting an alcohol of the formula $R_f$—$(CH_2)_n$—Q—$(CH_2)_h$—φ—[X—φ—]$_y$—$(CH_2)_m$OH with an acrylic acid of the formula $HOC(O)CR=CH_2$, or with its reactive derivative. The above alcohol can be obtained, for example, by converting the vinyl group of a styrene derivative having a $R_f$—$(CH_2)_n$$O(CH_2)_h$— group at the p-position to a 2-hydroxylethyl group. Such a $R_f$ group-containing styrene derivative is disclosed, for example, in the above-mentioned prior art references. Or, the alcohol wherein h is 0, such as $R_f$—$(CH_2)_n$—O—φ—[X—φ—]$_y$—$(CH_2)_m$OH, can be obtained by reacting $R_f$—$(CH_2)_n$Z wherein Z is a chlorine atom, a bromine atom or an iodine atom, with an alcohol containing a phenolic hydroxyl group, such as OH—φ—[X—φ]$_y$—$(CH_2)_m$OH, under a basic condition. The compound wherein Q is a sulfur atom can likewise be obtained from a corresponding compound having a HS-group.

The present invention also provides a polymer of the polyfluorohydrocarbon group-containing acrylate of the formula (1) or a copolymer of such an acrylate with other copolymerizable monomer, and a process for the production thereof.

The polyfluorohydrocarbon group-containing acrylate of the present invention can be polymerized by a method similar to a method for preparing known polyfluorohydrocarbon group-containing acrylates, to obtain a polymer including a homopolymer and a copolymer (hereinafter generally referred to as a polymer including a copolymer of two or more monomers). In such a case, as the polyfluorohydrocarbon group-containing acrylate of the present invention, a mixture of two or more compounds of different types may be employed. For example, it is preferred to use a mixture of two or more compounds differing only in the carbon number of the $R_f$ groups. It is particularly preferred to use a mixture of two or more perfluoroalkyl group-containing acrylates differing only in k of $CF_3(CF_2)_k$—.

The polymer may further be a copolymer of the polyfluorohydrocarbon group-containing acrylate of the present invention with various other copolymerizable monomers (hereinafter referred to as comonomers) copolymerizable with the acrylate of the present invention (the polymer of the monomer of the present invention with the comonomer will hereinafter be referred to as a copolymer). For the purpose of improving the physical properties of the polymer utilizing the characteristics of the monomer of the present invention, it is possible to obtain a better copolymer by adjusting the type and the amount of the comonomer. The comonomer is not particularly limited, and various comonomers may be used. It is further possible to use two or more comonomers in combination. Hereinafter, the term (meth)acrylate means both an acrylate and a methacrylate, and the same applies to the terms (meth)acrylic acid, (meth)acrylamide or the like.

The comonomer includes, for example, olefins, vinyl esters, halogenated vinyls, unsaturated carboxylic acids such as (meth)acrylic acid, (meth)acrylates, (meth)acrylonitriles, (meth)acrylamides, styrenes, vinyl ethers, unsaturated polybasic carboxylic acids, their anhydrides, unsaturated polybasic carboxylates such as esters, and polyfluorohydrocarbon group-containing monomers such as polyfluorohydrocarbon group-containing (meth)acrylates other than the polyfluorohydrocarbon group-containing acrylates of the present invention.

Preferred comonomers include (meth)acrylates, (meth)acrylamides, vinyl ethers and vinyl esters, which have a linear saturated alkyl group having at least 4 carbon atoms. Further, such comonomers may contain a functional group such as a hydroxyl group, an amino group, a sulfonic acid group or a carboxyl group. Further, a commonly copolymerizable ethylenic monomer such as vinyl chloride, ethylene, vinylidene chloride, vinyl fluoride, vinylidene fluoride or chlorotrifluoroethylene, may be employed.

When the monomer of the present invention and the comonomer are to be copolymerized, the proportion of the monomer of the present invention to the total monomers, is preferably at least the effective amount (usually about 2 mol %) to obtain the desired effects of the monomer of the present invention. The proportion is more preferably at least 10 mol %, most preferably at least 15 mol%. There is no particular upper limit, but from the viewpoint of a preferred use of the comonomer, the proportion is preferably at most 85 mol %, more preferably at most 75 mol %. Accordingly, the proportion of polymerized units of the monomer of the present invention in the polymer is most preferably at least 15 mol % to the polymerized total monomer units in the polymer.

With respect to the molecular structure, the polymer or the copolymer may be a random polymer obtainable by a usual radical polymerization method, or a block polymer or a graft polymer obtainable by a multi-stage polymerization. The molecular weight of the polymer or the copolymer is not particularly limited and may be selected within a wide range covering from an oligomer region of about 1,000 to a high polymer region of about 1,000,000. A preferred molecular weight is from 1,000 to 500,000.

The polymer of the present invention can be produced by using a common polymerization method such as a solution polymerization method using an organic solvent, a dispersion polymerization method using water as the dispersing medium or an emulsion polymerization method. As the emulsion polymerization method, not only a usual one step polymerization method but also a multi-stage polymerization such as a seed polymerization may be used without any particular restriction. One of the features of the polymer of the present invention is that it has a good affinity to a petroleum type hydrocarbon organic solvent. Thus, this polymer has an improved solubility to an organic solvent containing a large amount of a hydrocarbon type solvent, over conventional polymers. Accordingly, as a polymerization medium, such an organic solvent can be used, and in the agent containing this polymer, as described hereinafter, such an organic solvent can be used.

When the polymer or the copolymer (hereinafter, both will be generally referred to as the polymer) of the present invention is used as an agent, the polymer of the present invention may be used as it is, or may be used in the form of a solution, a dispersion or an emulsion. To such an agent, a polymer other than the polymer of the present invention or other additives may be incorporated. As the polymer other than the polymer of the present invention, a homopolymer or a copolymer of the above-mentioned comonomer may be mentioned. Further, it may be a condensed polymer or a compound capable of forming a condensed polymer. As the additives other than the polymer, a chemical agent such as a stabilizer or a surfactant as well as a solvent and a dispersant, may be mentioned.

The present invention provides the above-mentioned agent, particularly a water and oil repellant for fibers or a surface modifier containing the above-mentioned polymer as an effective component.

The polymer to be used as the water and oil repellant may be the polymer of the present invention alone, or a blend of at least two polymers containing the polymer of the present invention as the main component. As the polymer to be blended to the polymer of the present invention, any commonly used polymer or resin such as polyethylene, polystyrene, polyamide, polyester, polymethyl methacrylate or a silicone resin may be used without any particular restriction, since the polymer of the present invention is excellent in the compatibility with other polymers. Further, a composition comprising the polymer of the present invention and other polymer, is useful for a water and oil repellant, a surface modifier or other applications. The amount of the polymer of the present invention in such a composition is not particularly limited so long as it is an effective amount, with which the effects of the polymer of the present invention can be obtained.

The manner of use of the water and oil repellant and the surface modifier of the present invention is not particularly limited. For example, they may be applied to the surface of the objects to be treated in the form of the aqueous dispersion, the organic solvent dispersion or the solution as mentioned above, or the polymer obtained by the above-mentioned polymerization method may be kneaded into a resin.

The objects to be treated by the water and oil repellant and the surface modifier of the present invention are not particularly limited, and they may, for example, be fiber products such as natural or synthetic fibers and their mixed fibers, or articles such as metal, glass, resin molded products or resin films. Particularly, by the use of the polymer of the present invention, they may be developed for applications where high water and oil repellency and its lasting effects are required, such as worker's clothings, uniforms or filter materials. Further, they are applicable as surface modifies utilizing the low surface tension, the low friction and the low adhesiveness in addition to the water and oil repellency.

The monomer of the present invention contains, in its structure, a benzene ring which can readily be oriented at a molecular level, and it is believed that the orientation of the polyfluoroalkyl group located at its forward end is thereby facilitated, whereby the high surface modifying effects and their lasting effects can be accomplished. Further, as compared with the conventional polyfluoroalkylacrylate-type polymers, this polymer is capable of realizing adequate orientation of the polyfluoroalkyl group side chains even at a low fluorine concentration, whereby the affinity to an organic solvent or the compatibility with other resins, which used to be a problem with conventional polymers of this type, is improved.

Now, the present invention will be described in further detail with reference to Examples. However, it should be understood that the present invention is by no means restricted to such specific Examples. The following methods were employed for the evaluation of various physical properties.

Measurement of the melting point: Measured by a differential scanning calorimeter (DSC) in accordance with the method described in JIS K7121-1987.

Measurement of the dynamic contact angle: The dynamic contact angle of water at 25° C. to the polymer coated slide glass, was measured at a moving speed of 30 mm/sec by means of DCA-20 manufactured by Orientech Co.

Water repellency: JIS L1092

Oil repellency: AATCC 118-1978

Here, the symbol + attached to the numerical values for water repellency and oil repellency means that the actual values are slightly higher than the indicated numerical values, and the symbol—attached thereto means that the actual values are slightly lower than the indicated numerical values.

EXAMPLE 1

Into a 500 ml four-necked flask, 9.6 g (16.6 mmol) of n-$C_8F_{17}CH_2OCH_2$—$C_6H_4$—$CH=CH_2$ (wherein —$C_6H_4$— represents a p-phenylene group, and the same applies hereinafter) and 20 ml of dry THF (tetrahydrofuran) were charged and cooled to 0° C. Then, 1.5 ml of a borane-dimethylsulfide complex (10M) was gradually dropwise added thereto from a dropping funnel. The mixture was stirred at room temperature for 3 hours, and then 5 ml of water was gradually dropwise added thereto. Then, 20 ml of a 3M sodium hydroxide aqueous solution and 50 ml of a 30% hydrogen peroxide aqueous solution were added thereto, and the mixture was stirred overnight.

The organic layer was extracted with R-113 (1,1,2-trichlorotrifluoroethane), and then the solvent was distilled off to obtain 10.0 g of a crude product. This crude product was a mixture comprising a primary alcohol n-$C_8F_{17}CH_2OCH_2$—$C_6H_4$—$CH_2CH_2OH$ and a secondary alcohol n-$C_8F_{17}CH_2OCH_2$—$C_6H_4$—$CH_2(OH)CH_3$ at a molar ratio of 85/15. The crude product was recrystallized from hexane to obtain 5.4 g (9.2 mmol) of the primary alcohol having a purity of 95%.

Into a 100 ml four-necked flask, 5.4 g (9.2 mmol) of the obtained primary alcohol n-$C_8F_{17}CH_2OCH_2$—$C_6H_4$—$CH_2CH_2OH$, 20 ml of R-113 and 1.1 g of triethylamine were charged and cooled to 0° C. Then, 1.0 g of acrylic acid chloride was gradually dropwise added thereto, and the mixture was stirred at room temperature for 2 hours. The reaction solution was filtered by means of a glass filter. Then, the solvent was distilled off from the filtrate. The solid content was washed with water to obtain 4.0 g of a crude product. The crude product was recrystallized from ethanol to obtain 2.6 g (4.0 mmol) of the desired n-$C_8F_{17}CH_2OCH_2$—$C_6H_4$—$CH_2CH_2O$—$C(O)CH=CH_2$ (hereinafter referred to as "F8").

$^1$H-NMR(TMS, $CDCl_3$): 2.86 ppm(2H,t,J=7.1Hz), 3.95 (2H,t,J=10.0Hz), 4.40(2H,t,J=8.1Hz), 4.64(2H,S), 5.75–6.50(3H,m), 7.25(4H,S)

$^{19}$F-NMR($CFCl_3$,$CDCl_3$): −81.4 ppm(3 F,t,J=7.6 Hz), −119.8 ppm(2 F,S), −122.5–123.6 ppm(10 F,m), −126.6 ppm(2 F,S)

EXAMPLE 2

Into a 100 ml glass pressure reactor, 2.6 g of F8 prepared in Example 1, 20.0 g of R-113 and 0.07 g of azobisisobutyronitrile were charged and freeze-deaerated. Then, the gas phase was flushed with nitrogen, and polymerization was conducted at 65° C. for 12 hours. The obtained polymer was reprecipitated and purified by ethanol to obtain 2.1 g of a white fine powdery polymer. The polymer was subjected to the DSC measurement, whereby peaks corresponding to the melting points of the coherent structures of the side chain portions were observed at two points of 89° C. and 121° C. The molecular weight was found to be about 200,000 by weight average molecular weight as measured by GPC. Further, this polymer was added to THF in an amount corresponding to 5 wt %, whereupon it dissolved completely. This polymer will be represented by "P-F8" hereinafter. Likewise, symbols for other polymers will be presented by attaching P- in front of the symbols for the corresponding monomers.

EXAMPLES 3 to 6

Using the same method as in Example 1 except for the starting material, monomers represented by the following symbols were prepared instead of F8, and polymers were prepared by the same method as in Example 2 except that such monomers are employed, and the melting points of the crystal portions were measured. The molecular weights and the melting points of the crystals are shown in Table 1.

F7: n-$C_7F_{15}CH_2OCH_2$—$C_6H_4$—$CH_2CH_2O$—$C(O)CH=CH_2$

F10: n-$C_{10}F_{21}CH_2OCH_2$—$C_6H_4$—$CH_2CH_2O$—$C(O)CH=CH_2$

EPO: n-$C_3F_7O[CF(CF_3)CF_2O]_2CF(CF_3)CH_2OCH_2$—$C_6H_4$—$CH_2CH_2O$—$C(O)CH=CH_2$

F8H: n-$C_8F_{17}C_2H_4OCH_2$—$C_6H_4$—$CH_2CH_2O$—$C(O)CH=CH_2$

TABLE 1

| Polymer | | Weight average molecular weight (× 10$^5$) | Melting point of the crystal (°C.) |
| --- | --- | --- | --- |
| Example 3 | P-F7 | 1.8 | 50, 120 |
| Example 4 | P-F10 | 2.5 | 118, 125 |
| Example 5 | P-FPO | 0.9 | none |
| Example 6 | P-F8H | 2.0 | 70, 120 |

EXAMPLE 7

Into a 200 ml four-necked flask, 20.0 g (39.8 mmol) of n-$C_6F_{13}(CH_2)_4I$, 5.5 g (39.8 mmol) of 2-(4-hydroxyphenyl) ethyl alcohol, 2.0 g of sodium hydroxide and 50 ml of dry diglyme were charged and stirred at 100° C. for 4 hours. The reaction mixture was put into 500 ml of cold water, and then the solid substance was centrifugally separated. The obtained solid substance was washed with water to obtain 17.3 g (purity: 95%, yield: 84%) of n-$C_6F_{13}(CH_2)_4$—O—$C_6H_4$—$C_2H_4OH$.

Into a 100 ml four-necked flask, 15.0 g (29.2 mmol) of the obtained primary alcohol n-$C_6F_{13}(CH_2)_4$—O—$C_6H_4$—$C_2H_4OH$, 20 ml of R-113 and 3.3 g of triethylamine were charged and cooled to 0° C. Then, 2.9 g of acrylic acid chloride was gradually dropwise added thereto, and the mixture was stirred at room temperature for 2 hours. The reaction solution was filtered by a glass filter, and then the solvent was distilled off from the filtrate. The solid content was washed with water to obtain 12.0 g of a crude product. The crude product was recrystallized from methanol to obtain 8.9 g of the desired n-$C_6F_{13}(CH_2)_4$—O—$C_6H_4$—$C_2H_4OC(O)CH=CH_2$ (hereinafter referred to as "$F_6H_4$").

$^1$H-NMR(TMS, $CDCl_3$): 1.50–2.52 ppm(6H,m), 2.92(2H, t,J=7.07 Hz), 3.80–4.10(2H,m), 4.33(2H,t,J=7.15 Hz), 5.70–6.60(3H,m), 6.82(2H,d,J=8.95 Hz), 7.14(2H,d,J=8.95 Hz)

$^{19}$F-NMR($CFCl_3$,$CDCl_3$): −81.3 ppm(3 F,t,J=7.6 Hz), −114.9 ppm(2 F,broad S), −122.3 to −124.0 ppm(6 F,m), −126.7 ppm(2 F,broad S).

EXAMPLE 8

Into a 100 ml glass pressure reactor, 6.0 g of F6H4 prepared in Example 7, 20.0 g of R-113 and 0.09 g of azobisisobutyronitrile were charged and freeze-deaerated. Then, the gas phase was flushed with nitrogen, and polymerization was conducted at 65° C. for 12 hours. The obtained polymer was reprecipitated and purified by ethanol to obtain 5.7 g of a white fine powdery polymer. The polymer was subjected to the DSC measurement, whereby peaks corresponding to the melting points of the coherent structures of the side chain portions were observed at two points of 117° C. and 144° C. The molecular weight was found to be about 150,000 by weight average molecular weight as measured by GPC. Further, this polymer was added to THF in an amount of 5 wt %, whereupon it dissolved completely.

EXAMPLES 9 and 10

Using the same method as in Example 7 except for the starting material, monomers represented by the following symbols were prepared instead of F6H4, and polymers were prepared by the same method as in Example 8 except that such monomers were used, whereupon the melting points of the crystal portions were measured. The molecular weights and the melting points of the crystals are shown in Table 2.

F8H4: n-$C_8F_{17}(CH_2)_4$—O—$C_6H_4$—$CH_2CH_2$O—C(O)CH=$CH_2$

FPOH4: n-$C_3F_7$OCF($CF_3$)$CF_2$O$C_2F_4$—$C_4H_8$—O—$C_6H_4CH_2CH_2$O—C(O)CH=$CH_2$

TABLE 2

| | Polymer | Weight average molecular weight (× $10^5$) | Melting point of the crystal (°C.) |
|---|---|---|---|
| Example 9 | P-F8H4 | 1.8 | 127 |
| Example 10 | P-FPOH4 | 2.5 | 78, 140 |

EXAMPLE 11

Into a 300 ml four-necked flask equipped with a water separator, 15 g (100 mmol) of p-chloromethyl benzaldehyde, 7.4 g (120 mmol) of ethylene glycol, 0.8 g of p-toluene sulfonic acid and 100 ml of dry toluene were charged, and the mixture was stirred for 15 hours at a refluxing temperature of toluene, whereby about 2 ml of water was separated. From the reaction mixture, toluene was removed under reduced pressure, and then ethyl ether was added thereto. The organic layer was washed with a 1% sodium carbonate aqueous solution. The organic layer was dried, and then ethyl ether was distilled off under reduced pressure to obtain 18.4 g (purity: 94%, yield: 92%) of a liquid. The liquid was an acetal-modified product of p-chlorobenzaldehyde.

Into a 500 ml four-necked flask, 9.0 g of the obtained acetal-modified product, 20.4 g (45.3 mmol) of n-$C_8F_{17}CH_2$OH, 20 ml of a 30% sodium hydroxide aqueous solution, 50 ml of THF, 50 ml of R-113 and 2 ml of a 80% trioctylammonium chloride aqueous solution were charged and reacted at 60° C. for 20 hours. Then, 200 ml of water was added thereto, and the organic layer was separated. The aqueous layer was extracted with R-113, and the extract was added to the previous organic layer. To the organic layer, 150 ml of a concentrated aqueous hydrochloric acid solution was added, and the mixture was stirred for 30 minutes. Then, it was subjected to liquid separation, and the organic layer was removed to obtain 22.8 g of a fluorine-containing aldehyde n-$C_8F_{17}CH_2OCH_2$—$C_6H_4$—CHO (purity: 88%, yield: 89%).

The entire amount of this fluorine-containing aldehyde derivative was dissolved in 100 ml of THF, and 120 ml of a THF solution containing 5.5 g of p-aminophenylethyl alcohol was gradually added thereto, and the mixture was reacted at room temperature for one hour. THF was distilled off under reduced pressure, and the obtained solid substance was washed three times with methanol to obtain 20.4 g (yield: 74%) of a fluorine-containing imine derivative n-$C_8F_{17}CH_2OCH_2$—$C_6H_4$—CH=N—$C_6H_4$—$C_2H_4$—OH with a purity of 92.5%.

Into a 100 ml four-necked flask, 17.4 g (25.3 mmol) of the obtained fluorine-containing imine derivative n-$C_8F_{17}CH_2OCH_2$—$C_6H_4$—CH=N—$C_6H_4$—$C_2H_4$—OH 20 ml of R-113 and 3.8 g of triethylamine were charged and cooled to 0° C. Then, 2.5 g of acrylic acid chloride was gradually dropwise added thereto, and the mixture was stirred at room temperature for 2 hours. The reaction solution was filtered by means of a glass filter, and then the solvent was distilled off from the filtrate. The solid content was washed with water to obtain 18.0 g of a crude product. The crude product was recrystallized from methanol to obtain 16.1 g (21.7 mmol) (yield: 86%) of the desired n-$C_8F_{17}CH_2OCH_2$—$C_6H_4$—CH=N—$C_6H_4$—$C_2H_4$—OCOCH=$CH_2$ (hereinafter referred to as "F8IM").

$^1$H-NMR(TMS, $CDCl_3$): 3.0 ppm(2H,t), 4.00 ppm(2H,t), 4.40 ppm(2H,t), 4.75 ppm(2H,S), 5.75–6.55(3H,m), 7.15–7.35 ppm(2H,m), 7.45ppm(2H,d), 7.90 ppm(2H,d), 8.50 ppm(1H,s).

$^{19}$F-NMR(CFCl$_3$, $CDCl_3$, R-113): −81.3 ppm(3 F,t,J=7.6 Hz), −119.8 ppm(2 F,broad S), −122.3 to −124.0 ppm(10 F,m), −126.7 ppm (2 F, broad S).

EXAMPLE 12

Into a 100 ml glass pressure reactor, 3.0 g of F8IM prepared in Example 11, 3.0 g of methyl acrylate, 20.0 g of R-113 and 0.09 g of azobisisobutyronitrile were charged and freeze-deaerated. Then, the gas phase was flushed with nitrogen, and polymerization was conducted at 65° C. for 12 hours. The obtained polymer was reprecipitated and purified by ethanol to obtain 5.1 g of a white fine powdery polymer. The polymer was subjected to the DSC measurement, whereby a peak corresponding to the melting point of the cohesive structure of the side chain portion was observed at 96° C. The molecular weight was found to be about 80,000 by weight average molecular weight as measured by GPC.

EXAMPLE 13

Using the same method as in Example 11 except for the starting material, a monomer represented by the following symbol was prepared instead of F8IM, and a copolymer with methyl acrylate was prepared by the same method as in Example 12 except that such a monomer was used, whereupon the melting point of the crystal portion was measured. Its molecular weight and the melting point of the crystal are shown in Table 3.

F7IM: n-$C_7F_{15}CH_2OCH_2$—$C_6H_4$—CH=N—$C_6H_4$—$C_2H_4$—OCOCH=$CH_2$

TABLE 3

| | Polymer | Weight average molecular weight (× $10^5$) | Melting point of the crystal (°C.) |
|---|---|---|---|
| Example 13 | P-F7IM | 0.5 | 70 |

EXAMPLE 14

Into a 200 ml four-necked flask, 0.6 g of magnesium and 20 ml of dry THF were charged. Then, one drop of bromopropane was dropwise added thereto to activate magnesium. Then, 10 ml of a dry THF solution containing 5.1 g (16.9 mmol) of a t-butyldimethylsilyl etherified product of p-bromobenzyl alcohol, was dropwise added thereto from a dropping funnel while maintaining the reaction temperature at 30° C. After completion of the dropwise addition, the mixture was stirred at 30° C. for one hour. Then, 20 ml of a dry THF solution containing 9.6 g (16.9 mmol) of a fluorine-containing aldehyde n-$C_8F_{17}CH_2OCH_2$—$C_6H_4$—CHO obtained in Example 11, was gradually dropwise added thereto. The mixture was reacted at room temperature for 5 hours. Then, the reaction product was put into 200 ml of water and extracted with R-113. The solvent was distilled off to obtain 11.3 g of a crude product. The structure was analyzed, whereby it was found that a coupling product n-$C_8F_{17}CH_2OCH_2$—$C_6H_4$—CH(OH)—$C_6H_4$—$CH_2$OSi$(CH_3)_2$(t-Bu) was the main component.

Into a 500 ml four-necked flask, 11.3 g of the obtained coupling product and 100 ml of dry methylene chloride were charged, and 2.8 g of pyridinium chlorochromate was gradually added thereto. The mixture was reacted at room temperature for one hour. Then, 100 ml of a 5% sodium carbonate aqueous solution was added thereto, and the organic layer was separated. The organic layer was charged into a separately prepared flask equipped with a refluxing condenser, and 20 ml of THF and 20 ml of concentrated hydrochloric acid were added thereto. The mixture was reacted at 60° C. for 2 hours. The reaction product was cooled to room temperature, and R-113 was added thereto. Then, the organic layer was separated. After distilling the solvent off, the obtained solid substance was recrystallized from methanol to obtain 5.8 g of a primary alcohol n-$C_8F_{17}CH_2OCH_2$—$C_6H_4$—C(O)—$C_6H_4$—$CH_2OH$.

The obtained primary alcohol was converted to an ester n-$C_8F_{17}CH_2OCH_2$—$C_6H_4$—C(O)—$C_6H_4$—$CH_2OC(O)$ $CH=CH_2$ (hereinafter referred to as F8BP") (yield: 5.0 g) by acrylic acid chloride and triethylamine.

EXAMPLE 15

Into a 100 ml glass pressure reactor, 3.0 g of F8BP prepared in Example 14, 3.0 g of methyl acrylate, 20.0 g of R-113 and 0.09 g of azobisisobutyronitrile were charged and freeze-deaerated. Then, the gas phase was flushed with nitrogen, and polymerization was conducted at 65° C. for 12 hours. The obtained polymer was reprecipitated and purified by ethanol to obtain 4.8 g of white fine powdery polymer. The molecular weight was found to be about 85,000 by weight average molecular weight as measured by GPC.

EXAMPLE 16

Dynamic receding angle after immersion in warm water

The homopolymer of P-F8 obtained in Example 2 was dissolved in R-113 at 30° C. (solid content concentration: 1 wt %). While maintaining it at this temperature, the polymer solution was coated on a slide glass at a rate of 50 mm/min. This slide glass was subjected to hot air drying at 150° C. for 30 minutes, whereupon the receding angle of the dynamic contact angle of water measured by a Wilhelmy method (a dynamic contact angle measuring apparatus manufactured by Orientech Co.) at 25° C. was 97°. The polymer-coated slide glass was then immersed in constant temperature water at 40° C. for 10 hours and then dried an air, whereupon the dynamic contact angle of water was measured in the same manner, whereby the receding angle was 97°, and thus the initial water repellency was maintained.

EXAMPLE 17

Water and oil repellency of a water repellant-treated cloth

Using the same polymer solution as used in Example 16 (polymer concentration: 1 wt %), a polyester doeskin cloth, manufactured by Toray Industries, Inc. was treated, and curing was conducted at 150° C. for one minute, whereupon the water repellency and the oil repellency were evaluated and found to be 100 and grade 7, respectively. The treated cloth was immersed in constant temperature water at 40° C. for 10 hours and dried in air, whereupon the water repellency and the oil repellency were measured, whereupon the water repellency remained to be 100, and the oil repellency was 7-.

Further, using the same polymer solution, a span-like nylon cloth manufactured by Toray Industries, Inc. (20 cm ×20 cm) was treated, and curing was conducted at 180° C. for one minute, whereupon the water repellency was measured. The water repellency and the oil repellency at that time were 100 and grade 6, respectively.

To this fabric, ten drops of a soil prepared by liquid paraffin/cigarette ash (weight ratio: 10/1) were dropped, and abraded 70 times by a peeling tester (abrading load: 450 g/$cm^2$). Then, 20 drops of water were further dropped thereto, and the fabric was abraded 350 times (abrading load: 450 g/$cm^2$). The fabric was dried in air overnight, whereupon the water repellency was measured and found to be 70+. It was subjected to dry cleaning and then dried in air, whereupon the water repellency was measured, and it was found to be recovered to a level of 90.

EXAMPLE 18 and COMPARATIVE EXAMPLE 1

The treatment and evaluation (initial water repellency, water repellency after immersion in warm water, water repellency after the soil abrasion test, solubility) were conducted in the same manner as in Example 17 except that the polymer used was changed to those identified in Table 4. The results are shown in Table 4.

The symbols for the polymers used in Example 18 and Comparative Example 1 are as shown below. The molecular weights of the polymers and copolymers listed in Table 4 except for the polymers listed in Tables 1 and 2 are all about 200,000. The solubility represents the solubility of the polymer to THF when 5 wt % of the polymer was added to THF.

P-F8S: Copolymer of F8 with stearyl acrylate (molar ratio: 1/1)

P-F8SH: Copolymer of F8, stearyl acrylate and 2-hydroxyethyl acrylate (molar ratio: 48/50/2)

P-FA7: Polymer of n-$C_7F_{15}C_2H_4OC(O)CH=CH_2$

P-FA8: Polymer of n-$C_8F_{17}C_2H_4OC(O)CH=CH_2$

P-FS8: Polymer of n-$C_8F_{17}CH_2OCH_2$-$C_6H_4$—$CH=CH_2$

P-FS10: Polymer of n-$C_{10}F_{21}CH_2OCH_2$—$C_6H_4$—$CH=CH_2$

TABLE 4

| Polymer | Initial water repellency | water repellency after immersion in warm water | water repellency after the soil abrasion test | solubility |
| --- | --- | --- | --- | --- |
| Example 18 | | | | |
| P-F7 | 90 | 80+ | 70– | Dissolved |
| P-F10 | 100 | 100 | 70 | Swelled |
| P-F8H | 100 | 100 | 70 | Dissolved |
| P-F8S | 100 | 100 | 70– | Dissolved |
| P-F8SH | 100 | 90+ | 70 | Dissolved |
| P-F6H4 | 100 | 90+ | 70 | Swelled |
| P-F8H4 | 100 | 100 | 70 | Swelled |
| P-FPOH4 | 100 | 80+ | 70– | Dissolved |
| Comparative Example 1 | | | | |
| P-FA7 | 70 | 50– | 50– | Insoluble |
| P-FA8 | 90+ | 70 | 50– | Insoluble |
| P-FS8 | 80+ | 70– | 50– | Dissolved |
| P-FS10 | 100 | 90+ | 50– | Insoluble |

EXAMPLE 19

Polymer blend

A hexafluoroisopropanol solution having a solid content of 1 wt% containing P-F8/nylon 66 resin (weight ratio: 1/1) was prepared. The solution was transparent and homogeneous. In this solution, a slide glass was dipped and withdrawn, whereby a polymer blend coating film was prepared. This film was heat-treated at 200° C. for 30 minutes and then cooled, whereupon the dynamic contact angle of water was measured. The receding contact angle was 95°.

EXAMPLE 20

Polymer blend

A hexafluoroisopropanol solution containing 1 wt % of a solid content comprising P-F6H4/polyethylene terephthalate resin (weight ratio: 1/1) was prepared. The solution was transparent and homogeneous. In this solution, a slide glass was immersed and withdrawn, whereby a polymer blend coating film was prepared. This film was heat-treated at 150° C. for 30 minutes and then cooled, whereupon the dynamic contact angle of water was measured. The receding contact angle was 90°.

COMPARATIVE EXAMPLE 2

A polymer blend solution was prepared in the same manner as in Example 19 except that P-FA8 was used instead of P-F8. The solution was transparent at 40° C. but turbidified at room temperature. Using this solution, a polymer blend coating film was prepared on a slide glass in the same manner as in Example 19. The dynamic receding contact angle of water was measured and found to be 70°. Thus, the surface hydrophobic effects by the polyfluoroalkyl group were low.

EXAMPLE 21

A water-addition reaction was conducted in the same manner as in Example 1 except that 12.0 g (20 mmol) of n-$C_8F_{17}C_2H_4$—S—$CH_2$—$C_6H_4$—CH=$CH_2$ was used as the starting material, whereby 9.7 g of a crude product was obtained. This crude product was a mixture comprising a primary alcohol n-$C_8F_{17}C_2H_4$—S—$CH_2$—$C_6H_4$—CH=$CH_2$OH and a secondary alcohol n-$C_8F_{17}C_2H_4$—S—$CH_2$—$C_6H_4$—$CH_2$(OH)$CH_3$ it a ratio of 85/15 (mol %). The crude product was recrystallized from hexane to obtain 5.8 g (9.4 mmol) of the primary alcohol having a purity of 91%.

In a 100 ml four-necked flask, 5.8 g (9.4 mmol) of the obtained primary alcohol n-$C_8F_{17}C_2H_4$—S$CH_2$—$CH_2CH_2$OH was converted to an acrylic acid ester in the same manner as in Example 1. The crude product was recrystallized from ethanol to obtain 5.5 g (8.2 mmol) of the desired n-$C_8F_{17}C_2H_4SCH_2$—$C_6H_4$—$CH_2CH_2$O—C(O)CH=$CH_2$.

$^1$H-NMR(TMS, CDCl$_3$): 2.1–2.8 ppm(2H,m), 3.0(2H,t, J=7.0 Hz), 3.2–3.4(4H,m), 4.50(2H,t,J=7.0 Hz), 5.75–6.50 (3H,m), 7.25(4H,S)

$^{19}$F-NMR(CFCl$_3$,CDCl$_3$): −81.4 ppm(3 F,t,J=7.6 Hz), −119.8 ppm(2 F,S), −122.5 to −123.6 ppm(10 F,m), −126.6 ppm(2 F,S)

EXAMPLE 22

5.5 g of n-$C_8F_{17}C_2H_4SCH_2$—$C_6H_4$—$CH_2CH_2$O—C(O)CH=$CH_2$ (hereinafter referred to as "S-F8") prepared in Example 21, 20.0 g of R-113 and 0.09 g of azobisisobutyronitrile were added and polymerized in the same manner as in Example 2, and the polymer was purified to obtain 4.8 g of white powdery polymer. The polymer was subjected to the DSC measurement, whereby peaks corresponding to the melting points of the cohesive structures of the side chain portions were observed at two points of 82° C. and 125° C. The molecular weight was found to be about 150,000 by weight average molecular weight as measured by GPC.

Further, this polymer was added to tetrahydrofuran in an amount of 5 wt %, whereby it dissolved completely.

The monomer of the present invention contains a benzene ring which can readily be oriented at a molecular level to the portion which will be a side chain when formed into a polymer, whereby orientation of the polyfluoroalkyl group located at its forward end will be facilitated. Accordingly, it is believed that high surface modifying effects and their lasting effects can be accomplished as compared with a polymer of a conventional polyfluoroalkyl group-containing monomer.

Further, even at a relatively low fluorine concentration, adequate side chain orientation required for surface modification can be realized. Accordingly, the affinity to an organic solvent or the compatibility with other resins, which used to be a problem of conventional polymers of this type, will be substantially improved.

What is claimed is:

1. A polymer of at least one type of a polyfluorohydrocarbon group-containing acrylate of the formula (1):

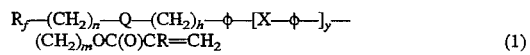

$$R_f—(CH_2)_n—Q—(CH_2)_h—\phi—[X—\phi—]_y—(CH_2)_mOC(O)CR=CH_2 \qquad (1)$$

wherein $R_f$ is a polyfluorohydrocarbon group having from 2 to 22 carbon atoms to which fluorine atoms are bonded, wherein some of such carbon atoms may be substituted by ether-type oxygen atoms, $\phi$ is a p-phenylene group which may be substituted by one or more halogen atoms selected from fluorine and chlorine, provided that when a plurality of $\phi$ are present in one molecule, such plurality of $\phi$ may be the same or different from one another, R is a hydrogen atom, a methyl group, a fluorine atom, a chlorine atom or a bromine atom, Q is a oxygen atom or a sulfur atom, X is a single bond, —CH=CH—, —N=CH—, —CH=N—, or —C(O)—, n is an integer of from 1 to 22, h is an integer of from 0 to 22, m is an integer of from 1 to 11, and y is an integer of from 0 to 5.

2. The polymer according to claim 1, wherein the acrylate is an acrylate of the formula (1)

wherein $\phi$ is a p-phenylene group having no substituent, R is a hydrogen atom or a methyl group, Q is an oxygen atom, n is an integer of from 1 to 4, h is an integer of from 0 to 2, m is an integer of from 2 to 4, and y is 0 or 1.

3. The polymer according to claim 1, wherein the acrylate is an acrylate of the formula (1)

wherein $R_f$ is a $C_{4-18}$ polyfluoroalkyl group wherein at least 80% in number of the hydrogen atoms of the corresponding non-substituted alkyl group are substituted by fluorine atoms, and some or all of the rest of hydrogen atoms, if any, are substituted by chlorine atoms.

4. The polymer according to claim 1, wherein the acrylate is an acrylate of the formula (1)

wherein $R_f$ is a $C_{6-14}$ linear perfluoroalkyl group.

5. The polymer according to claim 1, wherein the acrylate is an acrylate of the formula (1)

wherein $R_f$ is a $C_{6-18}$ perfluorooxalkyl group having at least one perfluorooxypropylene group.

6. The polymer according to claim 1, wherein the acrylate is an acrylate of the formula (1)

wherein X is —CH═N— or —C(O)—.

7. The polymer according to claim 1, wherein the acrylate is an acrylate of the formula (1) wherein $R_f$ is a $C_{6-14}$ linear perfluoroalkyl group, $\phi$ is a p-phenylene group having no substituent, R is a hydrogen atom or a methyl group, X is —CH═N— or —C(O)—, Q is an oxygen atom, n is an integer of from 1 to 4, h is an integer of from 0 to 2, m is an integer of from 2 to 4, and y is 0 or 1.

8. The polymer according to claim 1, where in said other monomers copolymerizable with the acrylate of the formula (1) are acrylates or methacrylates.

9. The polymer according to claim 1, wherein the ratio of the polymerized units of the acrylate of the formula (1) to the polymerized units of all monomers in the polymer is at least 15 mol %.

10. The polymer according to claim 1, which has a molecular weight of from 1,000 to 500,000.

11. The polymer of claim 1, wherein said polymer is of at least one type of the acrylate of the formula (I) with at least one other type of monomer copolymerizable with said acrylate of formula (I).

12. A water and oil repellent for fibers, which contains the polymer of claim 1 as an effective component.

13. A surface modifier which contains the polymer of claim 1 as an effective component.

14. A composition comprising the polymer of claim 1 and other polymer.

* * * * *